(12) United States Patent
Greco

(10) Patent No.: US 6,221,044 B1
(45) Date of Patent: Apr. 24, 2001

(54) AUTOMATIC INJECTION DEVICE

(76) Inventor: Ermanno Greco, Viale Liegi, 6-00192, Rome (IT)

( * ) Notice: Subject to any disclaimer, the term of this patent is extended or adjusted under 35 U.S.C. 154(b) by 0 days.

(21) Appl. No.: 09/171,946

(22) PCT Filed: Apr. 14, 1997

(86) PCT No.: PCT/IT97/00082

§ 371 Date: Oct. 29, 1998

§ 102(e) Date: Oct. 29, 1998

(87) PCT Pub. No.: WO97/41907

PCT Pub. Date: Nov. 13, 1997

(30) Foreign Application Priority Data

May 2, 1996 (IT) .............................................. RM96A0297

(51) Int. Cl.[7] .................................................. A61M 5/20
(52) U.S. Cl. ........................................... 604/134; 604/232
(58) Field of Search .................................. 604/131, 134, 604/135, 136, 148, 232, 234

(56) References Cited

U.S. PATENT DOCUMENTS

| 3,880,163 | * | 4/1975 | Ritterskamp | 128/218 |
| 4,006,849 | * | 2/1977 | Van Vroenhoven | 222/309 |
| 4,316,463 | * | 2/1982 | Schmitz et al. | 128/218 F |
| 4,710,178 | * | 12/1987 | Leonard et al. | 604/209 |
| 5,114,406 | * | 5/1992 | Gabriel et al. | 604/136 |
| 5,279,585 | * | 1/1994 | Balkwill | 604/207 |
| 5,279,586 | * | 1/1994 | Balkwill | 604/207 |
| 5,324,272 | * | 6/1994 | Smedley et al. | 604/193 |
| 5,358,489 | * | 10/1994 | Wyrick | 604/136 |
| 5,480,387 | * | 1/1996 | Gabriel et al. | 604/134 |

FOREIGN PATENT DOCUMENTS

| 9002220 | 3/1991 | (DE) . |
| 268191 | 5/1988 | (EP) . |
| 457135 | 11/1991 | (EP) . |
| 577448 | 1/1994 | (EP) . |
| 2138157 | 12/1972 | (FR) . |

* cited by examiner

Primary Examiner—Richard K. Seidel
Assistant Examiner—Cris Rodriguez
(74) Attorney, Agent, or Firm—Guido Modiano; Albert Josif; Daniel O'Byrne

(57) ABSTRACT

The present invention relates to improvements on automatic injection devices, in particular for self-administered drug therapies, providing for a high degree of internal stability of the syringe and, therefore, of the associated needle, thanks to a series of elastic wasp-waisted elements and a mobile tip made of a transparent material in the preferred embodiment, which besides enabling the regulation of the length of projection of the needle during the injection also allows the user to see the exact spot where the needle will enter the flesh.

10 Claims, 6 Drawing Sheets

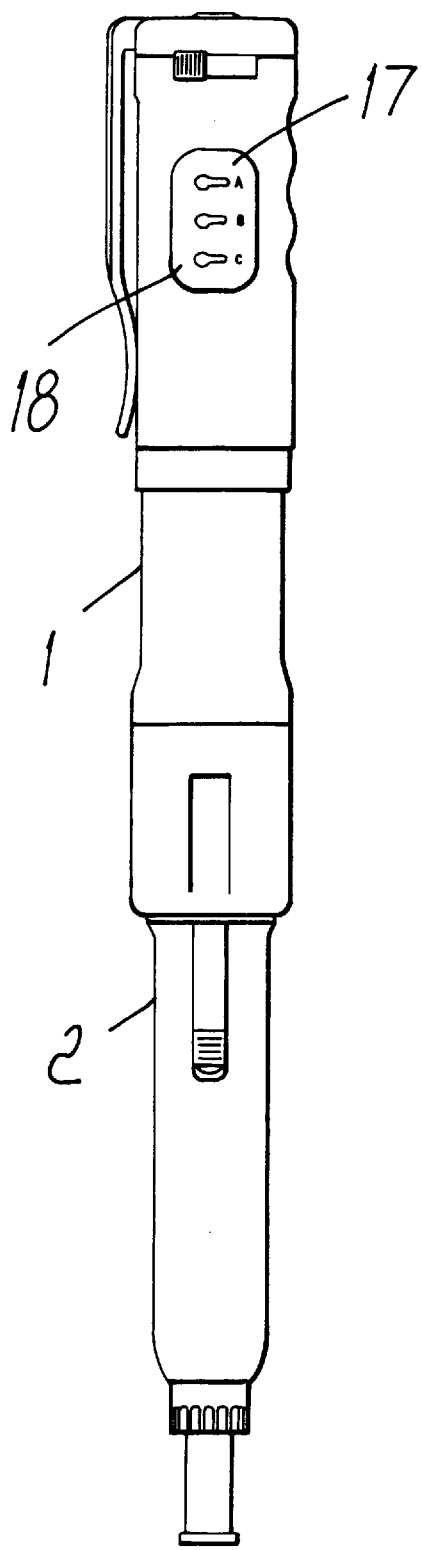
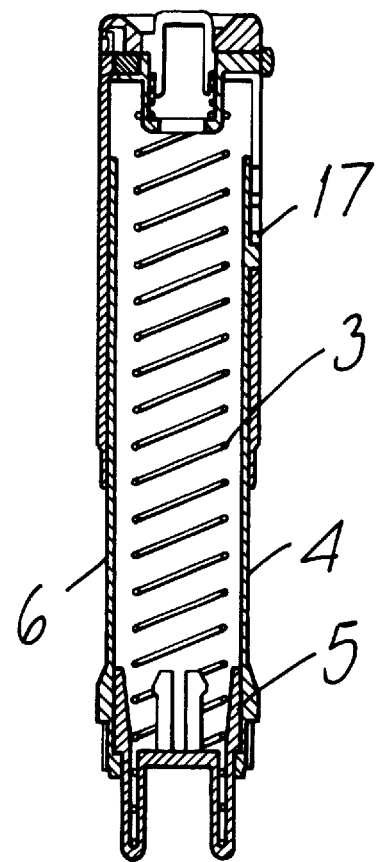
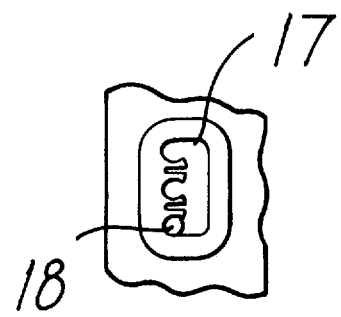
Fig. 5
Fig. 6

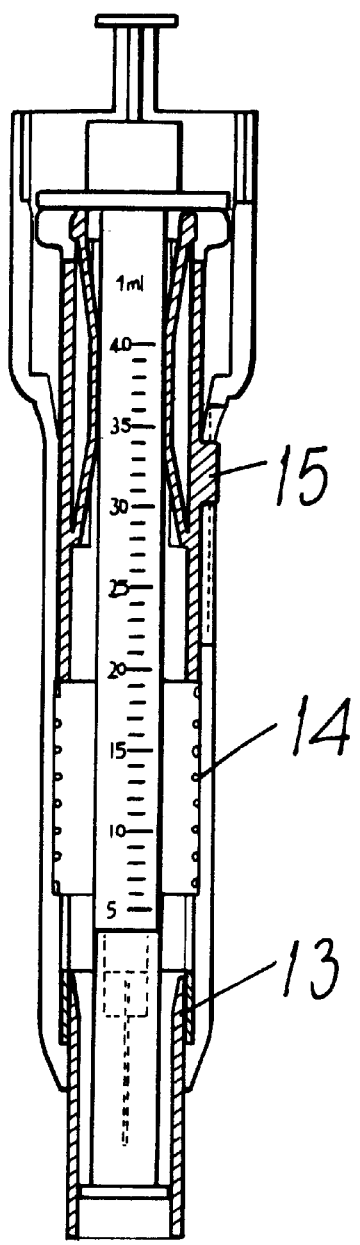
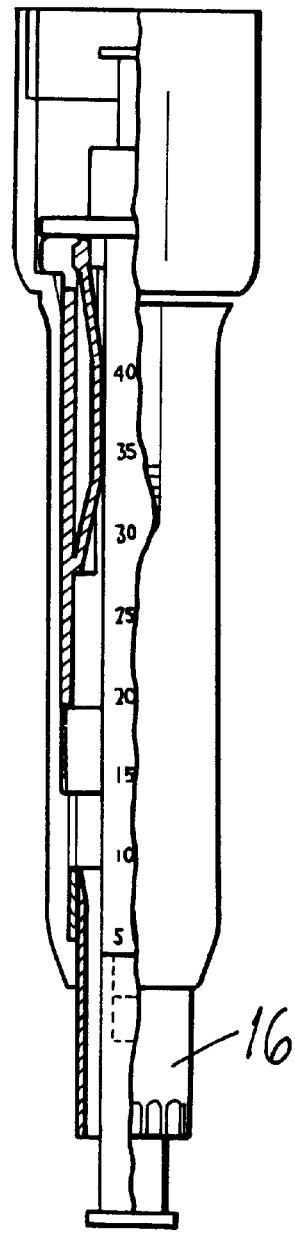
Fig. 11
Fig. 12

AUTOMATIC INJECTION DEVICE

BACKGROUND OF THE INVENTION

This invention relates to an automatic injection device, in particular for andrological use.

Automatic injection devices for self-administered drug therapies are currently known, especially for the treatment of erection disorders, where injection devices similar to pens are used to enable patients to self-inject vasoactive drugs directly into the cavernosum, in an extremely safe and simple manner.

Injection devices of the above mentioned type are the subject of previous patents and patent applications. The automatic injection device of U.S. Pat. No. 4,316,463 by William L. Schmitz comprises a barrel inside which there is a charged ampoule associated with a plunger and a needle. When the plunger is depressed the ampoule thrusts forward on the needle, which simultaneously projects from the barrel.

A similar technique is employed in the German model G 8333 718.0.

The automatic injection device of European patent 92304953.0 by Owen Munford Ltd employs a spring loaded drive member which thrusts forward on a charged capsule and a needle associated with the capsule, the needle projects from the device injects the drug and immediately after returns to the retracted position inside the device.

The injection device of European patent 87116619.5 by Wilhelm Haselmeier GmbH comprises a barrel housing a charged syringe, whose plunger is thrust forward by a piston depressed by a cylindrical body.

The injection device of Italian patent application RM92 A 000881 employs a spring loaded drive member which thrusts forward on the plunger of a charged syringe housed inside the device and ejects the drug through the needle.

The above mentioned injection devices feature several common characteristics, such as the barrel housing, a generally spring loaded internal mechanism, which, when activated, thrusts forward on the plunger of a charged syringe or capsule. Unfortunately, these injection devices also feature shortcomings which may be especially uncomfortable for the patient, such as an excessive bulkiness, especially with regard to the length; the impossibility to regulate the force of the spring loaded drive member which, when released, thrusts forward on the syringe plunger and the needle; the impossibility to regulate the length of the needle projecting from the device; the stability of the needle, which is not always guaranteed; and, last but not least, the excessive bulkiness of the injection devices which are currently available, to the detriment of what should be one of the key advantages of these devices: discretion.

SUMMARY OF THE INVENTION

According to the present invention there is provided an injection device comprising a barrel divided into two sections, the rear section is about ⅔ of the total length of the device, while the forward section is ⅓ of its length; the rear section houses the spring loaded drive member, a catch for holding the forward spring energized, a release mechanism for allowing said member to be sprung forwardly within the barrel, a plunger for ejecting the charge through the needle and devices for regulating the extension of the spring; the forward section of the injection device comprises a charged capsule housed inside a sleeve, the needle with a cap and the relative spring enabling the extraction of the needle and its return to the needle retracted position, after the removal of the needle cap; the button for removing the needle cap before using the syringe; the device for regulating the required needle length during the injection.

As mentioned above, one of the aims of the present invention is to reduce the bulkiness, and in particular the length, of the injection device when it is not in use, so that it may be carried inside a pocket with the utmost discretion. Therefore, the spring loaded drive member, the release mechanism and the spring extension regulating device, housed in the rear section, have been designed so as to occupy only a small part of this section, thus leaving sufficient room for introducing the forward section of the device, after it has been unscrewed and turned around, so as to considerably reduce the length of the injection device when it is not in use. The rear end of the forward section, containing the empty syringe, is closed by a jointed cylindrical cap.

As mentioned above, the spring loaded drive member which thrusts forward on the syringe plunger is housed in the rear section of the injection device, inside a cylindrical container co-axial with the barrel, at the rear end of which there is a housing for the syringe plunger head; the stroke of the cylindrical container may be regulated in three or more positions, by means of a pin running inside a toothed selector, thus making it possible to regulate the force by which the syringe plunger is thrust forward by the spring loaded drive member.

To regulate the needle projection length during the injection, the forward end of the injection device is provided with an adjustable mobile section, whose length may be increased or reduced, with regard to the barrel, to allow a shorter or longer portion of the needle, respectively, to project; in the preferred embodiment of the present invention the forward end of the infection device is made of a transparent material.

Obviously, an extremely important aspect enabling the correct working of the device is the stability of the syringe within the device, to keep the associated needle always in the correct position; to achieve this aim, the syringe housed in the rear end of the forward section of the device is held firmly in place, by a sleeve, co-axial with the barrel, substantially composed of a series of wasp-waisted elastic elements, which may adapt to the size of the syringe.

For a better understanding of the invention, the preferred embodiment will now be described in detail, with reference to the accompanying drawings, in which:

BRIEF DESCRIPTION OF THE DRAWINGS

FIGS. 5 and 6 show the mechanism for regulating the length of the spring loaded drive member, from the inside and the outside, respectively, in the maximum length position.

FIGS. 9–12 show the stages of assembly of the syringe in the forward section of the injection device.

DESCRIPTION OF THE PREFERRED EMBODIMENTS

Figure 1:
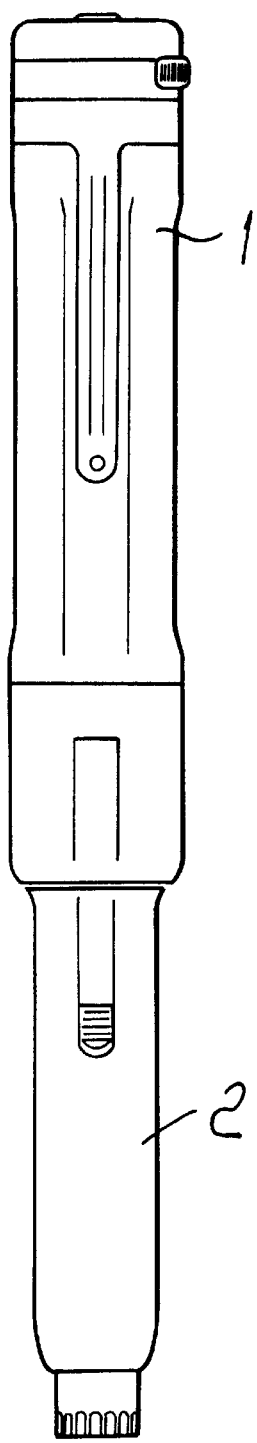
FIG. 1 shows the injection device when ready for use.
Figure 2:
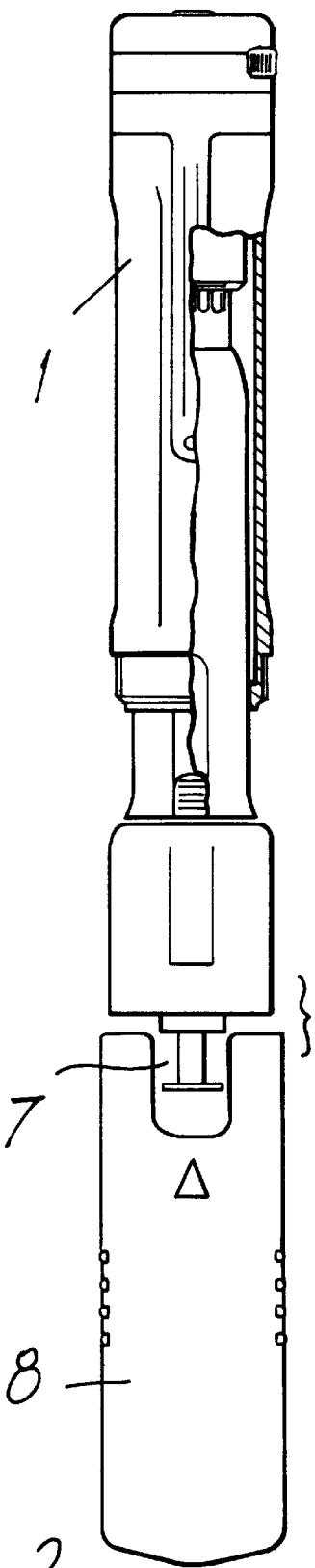
FIGS. 2–4 show the injection device in progressive stages of operation, from ready for use to closed.
Figure 3:
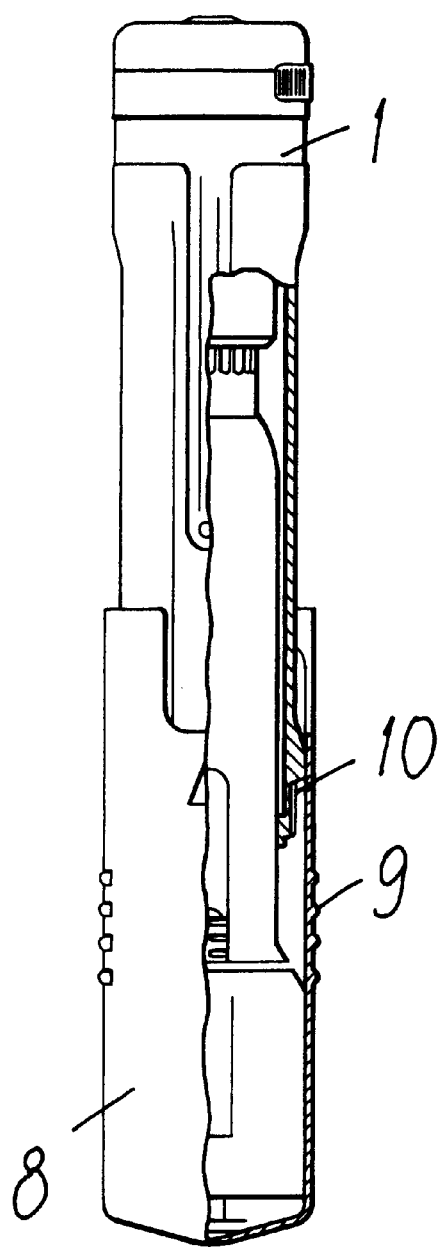
Figure 4:
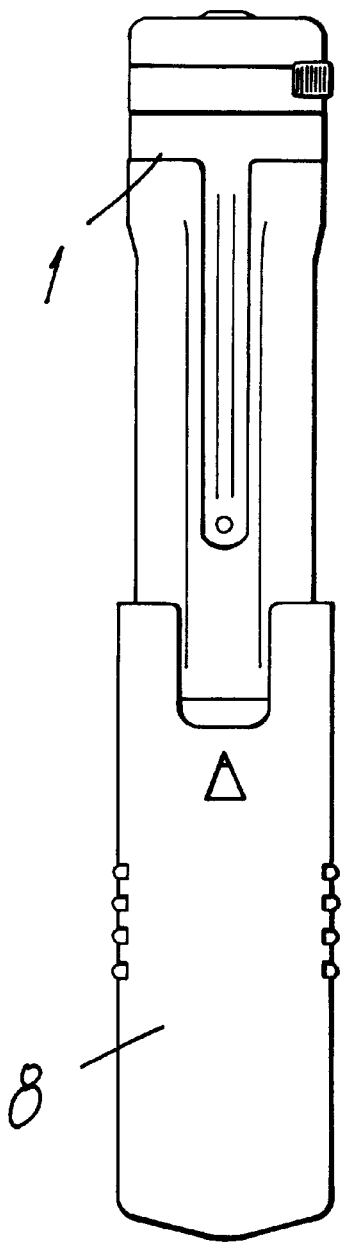
Figure 7:
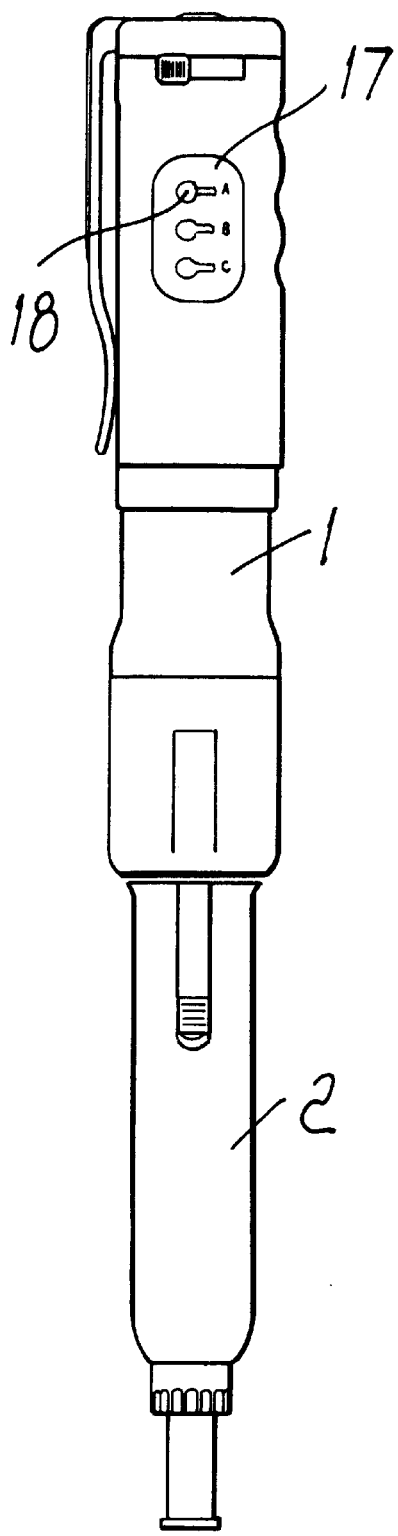
FIGS. 7 and 8 show the mechanism for regulating the length of the spring loaded drive member, from the inside and the outside, respectively, in the minimum length position.

With reference to the figures, the present injection device comprises a barrel divided into two sections, a rear section 1 and a forward section 2; the rear section 1 houses the spring loaded drive member 3 contained inside the cylinder 4, co-axial within the barrel 1, which at the forward end is integral with the annulus 5, into one side of which is introduced the head of the syringe plunger, while on the other side there is the catch 6 holding the forward spring energized; at the rear end of the rear section 1 there is the coupling and release mechanism, to which corresponds on the outside the release button; as mentioned above, when the spring is loaded, the assembly comprising the spring loaded drive member 3, the annulus 5 and the catch 6, occupy an extremely reduced space, therefore, the forward end of the rear section 1 is practically empty and capable of holding the forward section 2, which must be introduced forward end first; the syringe 7, housed inside the forward section 2, remains in its place and is protected by the cap 8, which is locked in the closed position by the clip 9 running inside the toothed selector 10.

To prepare the injection device for use, the forward section 2 is extracted from the rear section 1, the syringe is charged with the drug and screwed onto the rear section 1.

In the forward section 2, inside the sliding sleeve 12, there is a wasp-waisted elastic element for holding the syringe 7 firmly in place, even during the injection, and enabling the use of syringes of different sizes.

The sliding sleeve 12 also allows the removal of the cap 13 for protecting the needle before the injection: a spring 14 enables the sleeve to return to its home position when the control 15 is released.

The tip 16 at the forward end of the forward section 2 is adjustable, by known means such as a screw mechanism, so as to allow the regulation of the length of the projecting needle when in use; this characteristic makes it possible to better adapt the injection device to its various requirements. The tip 16 may be made of a transparent material, thus enabling the patient to view the exact point where the needle will enter the flesh.

Figure 8:
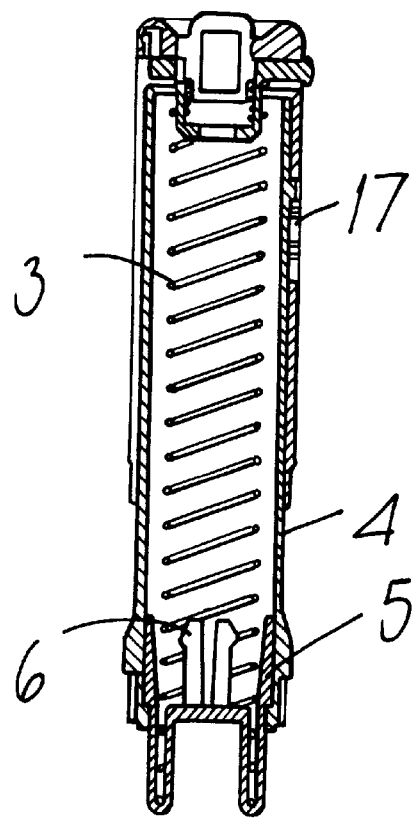
Figure 9:
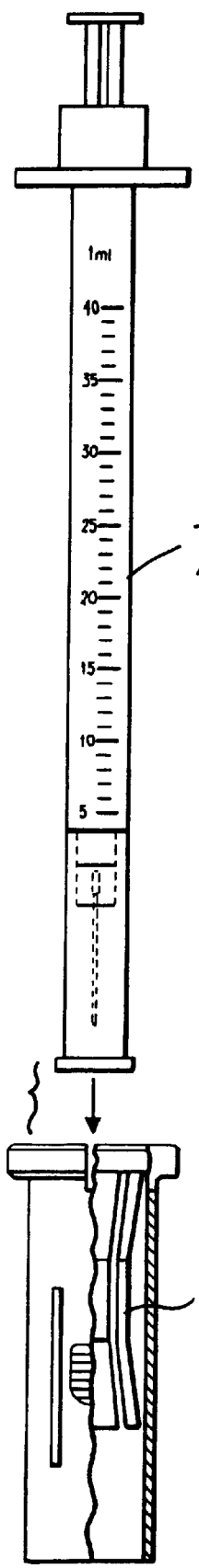
Figure 10:
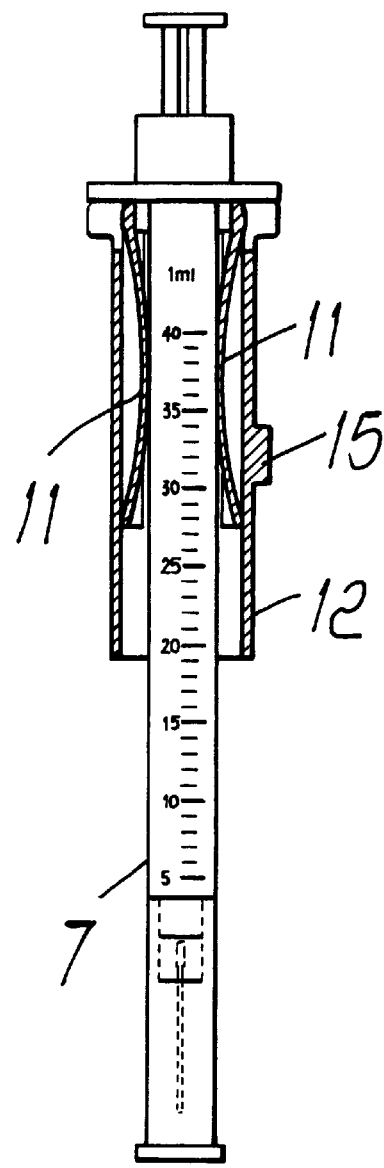

FIGS. 5 to 8 alternately show a full view and a longitudinal section of the rear section 1 of the injection device and FIGS. 6 and 8, in particular, show the device 17 enabling the regulation of the extension of the spring loaded drive member 3 and, therefore, of the force by which the annulus 5 thrusts forward on the syringe plunger when the member is released; as mentioned above, the member 3 is housed inside an internal cylinder 4 co-axial within the barrel and capable of sliding; the device 17 for regulating the extension of the spring loaded drive member 3 makes it possible to limit, for example, by means of a pin 18 passing between the outer barrel 1 and the inner barrel 4, which may be fixed in one of various positions so that, in the case shown in FIG. 6, the stroke of the inner barrel 4, fixed by means of the pin 18 in an intermediate position compared to the outer barrel 1, is longer than the stroke shown in FIG. 8, where the inner barrel 4 is fixed so as to touch the rear end of the outer barrel 1.

Obviously, different solutions may be adopted, rather than pins engaging in holes, for fixing the position of the inner barrel 4 compared to the outer barrel 1.

What is claimed is:

1. An automatic injection device comprising:
   an outer barrel divided into a rear section and a forward section, each of said rear and forward sections comprising a rear end and a forward end whereby in a use configuration of the injection device the rear end of said forward section is removably screwed to the forward end of said rear section, and each of said rear and forward sections being hollow, and said forward section has an outside dimension which is smaller than an inside dimension of said rear section;
   a syringe housed in said forward section such that a needle of said syringe is arranged adjacent the forward end of said forward section and a plunger of said syringe is arranged adjacent the rear end of said forward section;
   a spring loaded drive member comprising an annulus for engaging the plunger of said syringe in said use configuration and a catch for locking the drive member in an energized condition, said spring loaded drive member being housed in said rear section such that in said energized condition a spring element of said spring loaded drive member is energized and arranged substantially entirely adjacent the rear end of said rear section and such that said annulus of said spring loaded drive member is arranged adjacent the rear end of said rear section thereby to provide an empty space inside said rear section sufficient to allow said forward section to be unscrewed from said rear section and to be accommodated, in a non-use configuration of the injection device, inside said empty space with the forward end of said forward section arranged adjacent the rear end of said rear section;
   a cap for covering the rear end of said forward section in said non-use configuration of the injection device, said cap being provided with a catch for releasably attaching said cap to said rear section in said non-use configuration of the injection device to hold said forward section inside said rear section thereby for diminishing the bulk of the injection device in said non-use configuration with respect to said use configuration of the injection device;
   a cylinder slidably accommodated inside said rear section and having said annulus of said spring loaded drive member attached to an end of said cylinder for housing said spring loaded drive member in said rear section; and
   a pin selectively engageable in one of a plurality of holes provided in said cylinder and said rear section for selectively positioning said annulus in a selected position with respect to the forward end of said rear section for varying the stroke and thrust of said plunger of said syringe provided by said annulus of said spring loaded drive member in said use configuration of the injection device.

2. The injection device according to claim 1, further comprising a sliding sleeve for housing said syringe inside said forward section, said sliding sleeve being provided with an elastic sleeve element for selectively holding syringes of various sizes.

3. The injection device according to claim 1, wherein said rear section is longer than said forward section.

4. An automatic injection device comprising:
   an outer barrel divided into a rear section and a forward section, each of said rear and forward sections comprising a rear end and a forward end whereby in a use configuration of the injection device the rear end of said forward section is removably attached to the forward end of said rear section;
   a syringe housed in said forward section such that a needle of said syringe is arranged adjacent the forward end of said forward section and a plunger of said syringe is arranged adjacent the rear end of said forward section;
   a spring loaded drive member for engaging the plunger of said syringe in said use configuration; and a sliding sleeve for housing said syringe inside said forward section, said sliding sleeve being biased by a spring element in a home position towards said rear end of said forward section, and said sliding sleeve having a control element operable by a user to slide said sliding sleeve away from said home position towards said forward end of said forward section whereby said spring element causes said sliding sleeve to return to said home position upon release of said control element.

5. The injection device according to claim 4, further comprising an adjustable tip which is connected to the forward end of said forward section in an adjustable position for selecting the length of projection of the needle of said syringe with respect to the bottom of said adjustable tip.

6. The injection device according to claim 5 wherein said adjustable tip is made of a transparent material for viewing the needle of said syringe.

7. An automatic injection device according to claim 6, said siding sleeve being provided with an elastic sleeve element for selectively holding syringes of various sizes.

8. An automatic injection device comprising:

an outer barrel divided into a rear section and a forward section, each of said rear and forward sections comprising a rear end and a forward end whereby in a use configuration of the injection device the rear end of said forward section is removably attached to the forward end of said rear section, and each of said rear and forward sections being hollow, and said forward section has an outside dimension which is smaller than an inside dimension of said rear section;

a syringe housed in said forward section such that a needle of said syringe is arranged adjacent the forward end of said forward section and a plunger of said syringe is arranged adjacent the rear end of said forward section;

a spring loaded drive member comprising an annulus for engaging the plunger of said syringe in said use configuration and a catch for locking the drive member in an energized condition, said spring loaded drive member being housed in said rear section such that in said energized condition a spring element of said spring loaded drive member is energized and arranged substantially entirely adjacent the rear end of said rear section and such that said annulus of said spring loaded drive member is arranged adjacent the rear end of said rear section thereby to provide an empty space inside said rear section sufficient to allow said forward section to be removed from said rear section and to be accommodated, in a non-use configuration of the injection device, inside said empty space with the forward end of said forward section arranged adjacent the rear end of said rear section;

a cylinder slidably accommodated inside said rear section and having said annulus of said spring loaded drive member attached to an end of said cylinder for housing said spring loaded drive member in said rear section;

a pin selectively engageable in one of a plurality of holes provided in said cylinder and said rear section for selectively positioning said annulus in a selected position with respect to the forward end of said rear section for varying the stroke and thrust of said plunger of said syringe provided by said annulus of said spring loaded drive member in said use configuration of the injection device; and an adjustable tip which is connected to the forward end of said forward section in an adjustable position for selecting the length of projection of the needle of said syringe with respect to the bottom of said adjustable tip.

9. The injection device according to claim 8 wherein said adjustable tip is made of a transparent material for viewing the needle of said syringe.

10. The injection device according to claim 8, further comprising a cap for covering the rear end of said forward section in said non-use configuration of the injection device, said cap being provided with a catch for releasably attaching said cap to said rear section in said non-use configuration of the injection device to hold said forward section inside said rear section thereby for diminishing the bulk of the injection device in said non-use configuration with respect to said use configuration of the injection device.

\* \* \* \* \*